United States Patent [19]
Kuiper

[11] Patent Number: 6,148,235
[45] Date of Patent: Nov. 14, 2000

[54] IMPLANTABLE STIMULATOR WITH BATTERY STATUS MEASUREMENT

[75] Inventor: Edoardo C. Kuiper, Duiven, Netherlands

[73] Assignee: Vitatron Medical, B.V., Dieren, Netherlands

[21] Appl. No.: 09/118,706

[22] Filed: Jul. 17, 1998

[51] Int. Cl.$^7$ .................................................. A61N 1/378
[52] U.S. Cl. ............................................................ 607/29
[58] Field of Search .......................................... 607/9, 29

[56] References Cited

U.S. PATENT DOCUMENTS

| | | | |
|---|---|---|---|
| 4,231,027 | 10/1980 | Mann et al. .............................. | 340/636 |
| 4,345,603 | 8/1982 | Schulman ................................. | 607/29 |
| 4,448,197 | 5/1984 | Nappholz et al. ......................... | 607/29 |
| 4,606,350 | 8/1986 | Frost ................................. | 128/419 PG |
| 5,137,020 | 8/1992 | Wayne et al. .............................. | 607/29 |
| 5,620,474 | 4/1997 | Koopman ................................. | 607/29 |

*Primary Examiner*—Carl H. Layno
*Attorney, Agent, or Firm*—Thomas F. Woods; Michael J. Jaro; Harold Patton

[57] ABSTRACT

There is provided an implantable device system such as a battery-powered pacemaker system, with an improved capability of measuring battery internal impedance, thereby providing the means to determine anticipated device End of Life. Within one pacemaker cycle following a sensed beat or a delivered stimulus, and before delivery of a next stimulus, three battery measurements are taken at equally spaced time intervals. Due to the RC nature of the battery internal impedance, the first two battery voltage measurements can be used to calculate what the voltage would be at the third time, assuming no change in current load. At the third time, a predetermined incremental current load is added, and the battery voltage at the time of the added current load is measured. The voltage differential between the calculated battery voltage and the measured battery voltage at the third time, together with the predetermined incremental current load, is used to calculate the battery impedance.

15 Claims, 2 Drawing Sheets

IMPLANTABLE STIMULATOR WITH BATTERY STATUS MEASUREMENT

FIELD OF THE INVENTION

This invention relates to implantable stimulator devices, and particularly implantable pacemakers having circuitry for measuring battery impedance so as to determine the battery status and remaining device lifetime.

BACKGROUND OF THE INVENTION

Implantable cardiac pacemakers and other implantable devices are powered by batteries that have a finite energy capacity, such that it becomes important to monitor the status of the battery to determine remaining lifetime of the device. A typical battery, such as a lithium iodide-type battery used in implantable pacemakers has a given starting energy capacity, e.g., in the range of 600 mAh to 1800 mAh. The effective lifetime of the device is a function of the operating conditions, e.g., the parameters of the stimulus pulses and the effective output load. It is, of course, important to know when the battery is almost depleted, or empty, in order to safely replace the implanted pacemaker. As is known, it is not possible to replace only the battery, which is sealed within the case of the device, but rather the entire pacemaker must be replaced. Thus, it has been a longstanding concern of the pacemaker industry, and the implantable device industry generally, to provide an accurate indication of battery status, so as to predict when replacement may be needed.

A standard technique that has been used in pacemakers for determining the status of the battery is to measure the battery impedance. For various battery models, the characteristic of battery impedance as a function of remaining lifetime is known. Thus, the battery impedance, when it is accurately measured, provides an accurate indication of energy used, and consequently of remaining energy. A direct battery voltage measurement thus provides an actual operating parameter from which the battery status can be determined. Although not a control part of this invention, once the battery status has been determined, effective end of life (EOL) can be calculated based upon the current and projected rate of energy consumption. See U.S. Pat. No. 5,620,474, assigned to Vitatron Medical, B.V., and incorporated herein by reference.

In a typical prior art system, impedance is calculated either in response to an exterior programmer, or automatically, on the basis of a voltage difference ($\Delta U$) measured by the pacemaker. The pacemaker determines the $\Delta U$ value by taking two voltage measurements across the battery, one during which the normal pacemaker circuitry is connected across the battery and the other at a time when a defined additional battery load ($\Delta I$) is applied. Based on Ohms law, the battery impedance, $Z_I$ can be calculated as $$Z_I = \Delta U / \Delta I$$

A condition, and consequently a problem with this straightforward approach, is that for the two measurements, battery voltage should be affected only by the additional load, $\Delta I$. However, this rarely the case. For a pacemaker, the procedure is generally to take the two measurements at the same moment in successive pacemaker cycles, in order to make a best effort to have similar normal circuit loads on the battery for the two measurements. However, the fact is that battery voltage is continuously varying because of the changing battery condition after each pacemaker cycle, e.g., by variables such as energy consumption due to delivery of a stimulus and the effective load of the lead. As discussed below, it is known that the equivalent circuit of a battery is approximately that of an RC circuit, such that directly following a delivered stimulus, the battery output voltage drops, and rises exponentially thereafter. Consequently, from cycle to cycle, there will be battery output voltage variations depending upon whether a stimulus was delivered. In particular, for dual chamber pacemakers there can be substantial variations depending upon the sequence of pacing or not pacing in the different heart chambers.

In view of the above, there is a need in the implantable battery-powered device area for a more reliable way to measure battery impedance, and thus determine battery status. The improvement must take into account, and effectively eliminate, normal variations of battery voltage and pacemaker circuit load which may occur cycle-to-cycle, in order to improve the reliability of an impedance measurement based on inserting a defined extra current load for one of the battery measurements.

SUMMARY OF THE INVENTION

It is a primary object of this invention to provide an implantable device, particularly an implantable pacemaker, with circuitry for measuring battery impedance under conditions which are not affected by unwanted cyclical changes in current load. In the preferred pacemaker embodiment, it is an object to perform battery measurements between delivered pacing pulses, so that the measurements are not affected by changed battery conditions following generation of a pace pulse.

In accordance with the above object, there is provided a pacemaker system having measurement circuitry for carrying out a series of battery measurements intra-cardiac cycle, i.e., between delivered pace pulses. The measurements take advantage of the fact that battery voltage following delivery of a pace pulse recovers substantially exponentially, due to the RC nature of the internal battery impedance. A series of equally spaced measuring times are calculated, at each of which voltage across the battery output is measured. At the last of the measuring times, a predetermined additional current load is switched across the battery, producing an incremental voltage drop. The value that the battery voltage would have otherwise been when the current load is switched across its output is calculated based upon the prior measurements in view of the exponential rise of battery voltage, enabling determination of $\Delta V$ corresponding to $\Delta I$. Following this, battery impedance is calculated from the incremental voltage drop due to the known incremental current.

DESCRIPTION OF THE PREFERRED EMBODIMENTS

Figure 1:
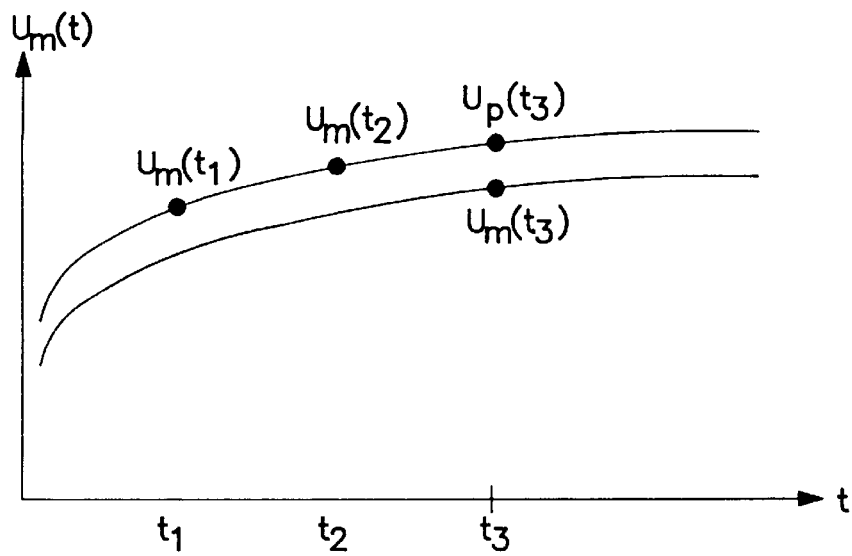
FIG. 1 is a series of curves illustrating the exponential recovery of battery voltage following delivery of a stimulus pulse, and also illustrating the incremental change in battery voltage when an incremental current load is added across the battery.

Referring now to FIG. 1, there is shown a set of curves which indicate the principle upon which the improved measurement circuit and method of this invention are based. The voltage across the device battery, indicated as $U_m(t)$, is shown plotted with respect to time, where 0 time represents the moment just after delivery of a stimulus pulse. Due to the fact that the internal impedance of a battery can be expressed as an equivalent RC circuit, the battery voltage drops at time of delivery of the stimulus pulse, and then rises exponentially. Calculation of battery impedance, and thus remaining battery capacity, is done by taking measurements at equally spaced times within one pacemaker cycle, e.g., at three equally spaced times indicated at $t_1$, $t_2$, and $t_3$ in FIG. 1. Due to the exponential nature of the voltage curve, and the equal spacing of the measurement times, the voltage at $t_3$, $U_p(t_3)$, can be calculated in accordance with the following formula:

$$U_m(t_2)/U_m(t_1) = U_p(t_3)/U_m(t_2)$$

Although, of course, $U_p(t_3)$ can be calculated strictly according to the logarithmic function, this simple calculation saves processor time and enables accurate determination of the value at time $t_3$, assuming no change in load on the battery. It is to be noted that, in order to reduce the variations of the battery voltage to an absolute minimum during the measurement cycle, it is preferable to keep the pacemaker microprocessor running, and not put it to "sleep" until $t_3$.

Still referring to FIG. 1, at time $t_3$ a predetermined precise current load $\Delta I$ is switched across the battery, causing a drop in the battery output voltage due to the battery internal impedance $Z_I$. This results in a battery voltage at $t_3$ as indicated, $U_m(t_3)$.

With the $U_p(t_3)$ and $U_m(t_3)$ information, $Z_I$ can now be calculated as follows:

$$Z_i = \Delta U / \Delta I$$

$$Z_i = \frac{U_p(t_3) - U_m(t_3)}{\Delta I}$$

$$Z_i = \frac{[U_m(t_2)/U_m(t_1)]U_m(t_2) - U_m(t_3)}{\Delta I}$$

Figure 2:
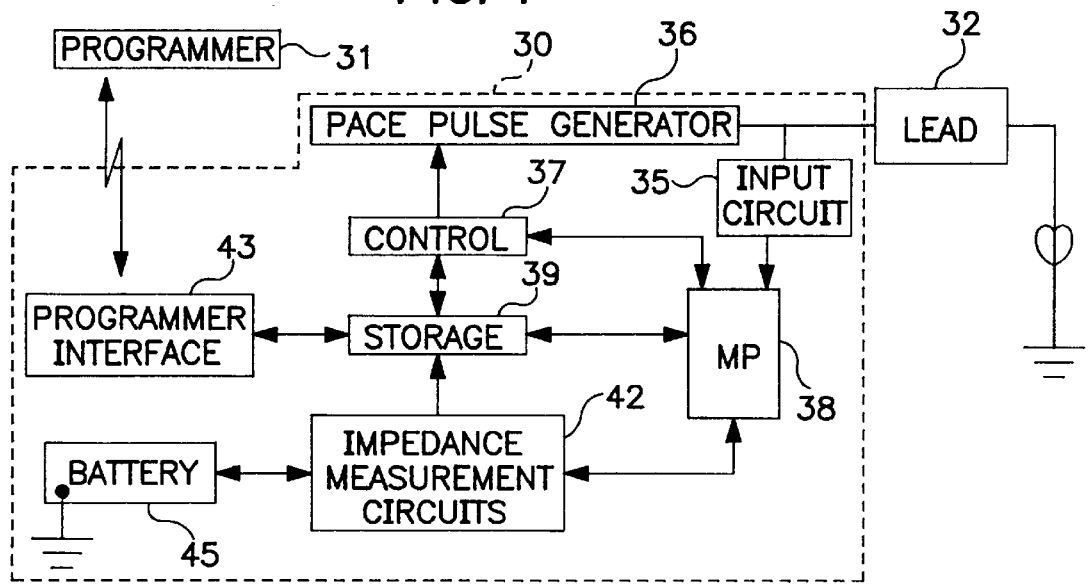
FIG. 2 is a block diagram showing the primary functional components of a pacing system of a preferred embodiment of this invention.

Referring now to FIG. 2, there is shown a circuit diagram of the primary components of a pacemaker which utilizes the impedance measurement and method of this invention in a preferred embodiment. An implantable pacemaker 30 is shown in combination an external programmer 31, and a lead 32 for delivering signals between the pacemaker and the patient's heart. The components of the pacemaker illustrated in this figure are only those pertinent to carrying out the subject invention, and it is understood that a functioning implantable pacemaker has a great many different components, as well as stored software, which are not specifically illustrated. See, for example, U.S. Pat. Nos. 5,247,930 and 5,350,411, incorporated herein by reference, illustrating in more detail the primary components of an exemplary implantable pacemaker.

The pace pulse generator 36 delivers pace pulses, under influence of control circuitry 37, for delivery through lead 32 to the patient's heart. Control 37 controls pace pulse parameters such as output voltage and pulse duration; in the exemplary embodiment of this invention, output voltage settings may be 1.3, 2.7, 4.0, 5.3 and 8.0 volts, and pulse widths can be programmed in 25 microsecond steps, within a range of 0.1 ms to 1.0 ms. While only a single pulse generator is illustrated, it is to be understood that both atrial and ventricular pace pulses may be generated each cycle; and, indeed, in a four-chamber pacing system, four pace pulses may be generated each cycle. Of course, for more than single chamber pacing the measurements must be taken before generation and delivery of a next pacing pulse. Control circuitry 37 acts under the influence of microprocessor 38 and information from storage 39. Storage 39 may suitably be RAM storage associated with the microprocessor subsystem. Detected signals from the patient's heart are processed in Input circuit 35, and forwarded to microprocessor 38 for use in logic and timing determination, in a known manner. Programmer 31 communicates with programmer interface block 43, to obtain data which is transferred to storage 39, for use in changing pacing conditions, and undertaking tasks such as impedance measurement. For example, the programmer can be used to initiate a lead impedance measurement, which is a standard pacemaker system operation. The lead impedance is an important parameter for determining pacemaker EOL, since it impacts ongoing energy consumption. Also, programmer 31 can be utilized to initiate a battery impedance measurement sequence.

The implantable pacemaker is powered by a battery 45, which supplies electrical power to all of the electrically active components of the pacemaker. Block 42 also contains an impedance measurement circuit, described in more detail in connection with FIG. 3, which measures the battery impedance either on programmer command or automatically on a periodic basis, under control of microprocessor 38.

Figure 3:
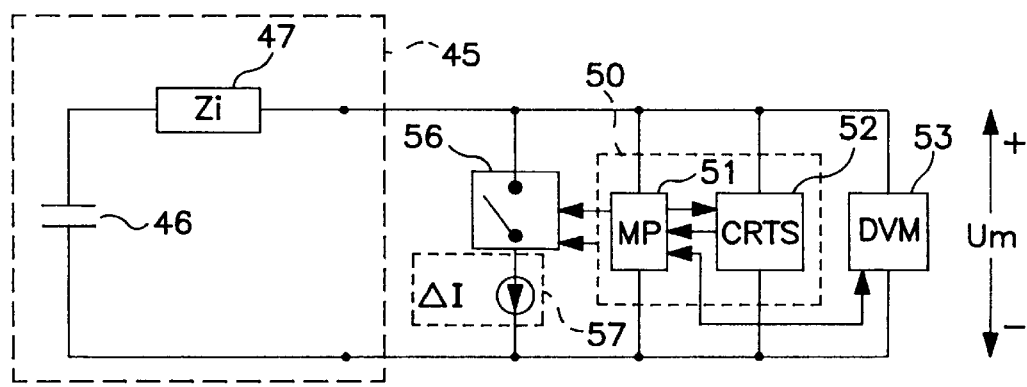
FIG. 3 is a circuit diagram of the primary components utilized for impedance measurement in a preferred embodiment of this invention.

Referring now to FIG. 3, there is shown in some detail the pacemaker circuitry for measuring battery voltage at the series of times illustrated in FIG. 1. The battery 45 is illustrated as having an ideal voltage source 46, in series with an impedance $Z_I$, designated at 47. As stated above, $Z_I$ is substantially a resistive-capacitive (RC) circuit. Shown connected across the battery terminals is a pacemaker circuit 50, comprising a microprocessor and associated memory indicated at 51, and all of the other functional pacemaker circuits indicated at 52. For purposes of this discussion, it is assumed that during the time period between delivered stimulus pulses, the normal current load drawn by circuitry 50 is substantially constant. Also shown is a digital volt meter 53, used to measure battery output when enabled to do so by a signal from microprocessor 51. And, important to this invention, the microprocessor controls switch 56 to place a current source 57 in circuit with the battery at time $t_3$ adding an additional load of $\Delta I$.

Figure 4:
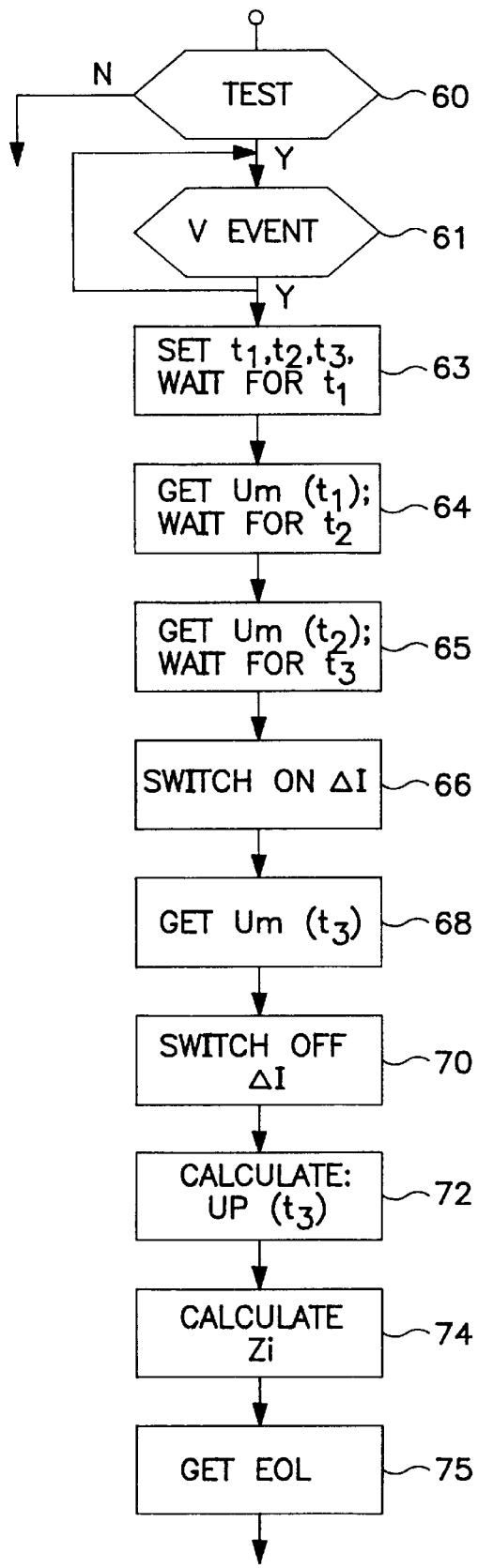
FIG. 4 is a flow diagram showing the primary steps carried out in an implanted device, in accordance with one embodiment of the system and method of this invention, for obtaining a measurement of battery impedance and device EOL.

Referring now to FIG. 4, there is shown a flow diagram of steps controlled preferably by microprocessor 51 and associated memory, for carrying out the battery impedance measurement. At 60, it is determined whether the pacemaker is to carry out a test to measure battery impedance. The test can be enabled either in response to a programmed signal from external programmer 31, communicated through programmer interface 43; or can be done periodically, e.g., once a day, based upon an internal device clock. If a test is indicated, at 61 the pacemaker waits for the end of the cycle, indicated as a ventricular event. When such an event, e.g., a delivered pace pulse has occurred, at block 63 the pacemaker sets timers to time out times $t_1$, $t_2$, and $t_3$. The timers are suitably part of circuits 52, and are set upon delivery of the pacing pulse (or sensing of a ventricular sense) under control of microprocessor 51. The pacemaker then waits for the first of the series of times, $t_1$.

At block 64, at time $t_1$ the microprocessor sends a signal to the voltmeter, and battery voltage $U_m(t_1)$ is measured and stored; and the pacemaker waits for the timeout of $t_2$. At block 65, at time $t_2$ the pacemaker gets and stores voltage $U_m(t_2)$ and waits for time $t_3$. At time $t_3$, the pacemaker switches on the additional load $\Delta I$, as indicated at 66, and then measures battery voltage, $U_m(t_3)$ as shown at 68. By following this, at 70, the load $\Delta I$ is switched off; and at 72 the pacemaker calculates $U_p(t_3)$, according to the above formula. All of the required measurements now having been taken, at 74 battery impedance $Z_I$ is calculated. At 75, the pacemaker calculates EOL, based on the measured battery impedance and projected ongoing device current consumption. The EOL can be obtained by the physician by interrogating the pacemaker with programmer 31.

It is to be noted that the preferred embodiment involves three measurement times, since this enables the simplest way of accurately determining $U_p(t_3)$. However, other patterns of measurements can be made within the scope of the invention, e.g., more than three measurements within the pacemaker cycle. However, the preferred embodiment of three equally time-spaced measurements between delivery of stimulus pulses enables the simplest way of determining Zi, while achieving the desired reliability.

What is claimed is:

1. An implantable device for generating and delivering stimulus pulses to a location in a patient's body, having a battery which provides energy to said device, said battery having an internal impedance which changes with cumulative expenditure of energy, a controllable pulse generator for generating said stimulus pulses, said device further having impedance means for measuring said battery impedance, said impedance means comprising:

voltage means for measuring the voltage output of said battery;

timing means operative following a delivered stimulus pulse for timing a sequence of measuring times which occur before a next delivered stimulus pulse;

a predetermined test load, and connecting means for connecting said test load across said battery at one of said measuring times of said sequence;

triggering means for triggering said voltage means to measure said battery voltage output at each of said measuring times; and calculating means for calculating the battery impedance as a function of the battery voltages measured at each of said measuring times.

2. The device as described in claim 1, wherein said timing means comprises means for timing out three of said measuring times which have equal time intervals therebetween, and wherein said connecting means connects said test load so that it is connected across said battery during the third of said measuring times.

3. The device as described in claim 2, wherein said calculating means comprises said microprocessor circuit, and said calculating means further comprises means for calculating from the first two of said measurements a projected value that said battery voltage would be at the time of said third measuring time in the absence of said test load.

4. The device as described in claim 1, wherein said device is an implantable pacemaker, said pacemaker having a normal circuit load connected across said battery between generation of pulses, and said timing means has means for referencing said sequence of measuring times with respect to a delivered stimulus pulse so that all measurements taken during a said sequence occur before a next delivered stimulus pulse.

5. The device as described in claim 4, comprising a microprocessor circuit, and wherein said microprocessor circuit controls said timing means, said triggering means and said connecting means.

6. The device as described in claim 1, wherein said test load comprises a current circuit for changing the current output from said battery by a predetermined amount.

7. A method of determining a measure of the impedance of a battery in an implanted device, said device having a normal circuit load and means for generating and delivering stimulus pulses, said method comprising:

taking a series of voltage measurements across said battery while it is connected across said normal circuit load, and timing said series to occur following a sensed beat or a delivered stimulus pulse and before delivery of a next said stimulus pulse;

placing of a predetermined additional current load across said battery during one of said series of measurements; and calculating said battery impedance from said voltage measurements and said additional current load.

8. The method as described in claim 7, comprising taking a series of three of said voltage measurements, and calculating from the first two of said measurements a projected value of battery voltage at the time of the third said measurement, and placing said predetermined additional current load across said battery during said third measurement.

9. The method as described in claim 8, wherein the time interval between said first and second and said second and third measurements is substantially equal.

10. The method as described in claim 9, comprising obtaining the difference between the projected voltage measurement at the third time and the measured voltage measurement at the third time.

11. The method as described in claim 10, comprising determining a measure of device End of Life as a function of said calculated battery impedance.

12. The method as described in claim 7, wherein said implanted device is a cardiac pacemaker, and said taking comprises taking three voltage measurements equally spaced timewise across said battery during a time interval which is free of a generated stimulus pulse.

13. The method as described in claim 12, comprising externally programming said pacemaker to initiate the determining of a measure of battery impedance.

14. The method as described in claim 12, comprising automatically initiating said determining of a measure of said battery impedance.

15. A battery-powered pacemaker, comprising:

voltage measuring means for measuring voltage across said battery;

means operative between delivery of stimulus pulses for determining expected battery voltage at a given time after a sensed beat or delivery of a stimulus pulse;

means for introducing a predetermined extra current load across said battery at said given time and for triggering said voltage measuring means to measure battery voltage at said given time; and calculating means for determining the impedance of said battery from said expected battery voltage, said measured battery voltage and said extra current load.

* * * * *